March 9, 1943. M. B. CRANE Plant Pat. 571
BLACKBERRY PLANT
Filed Oct. 20, 1942
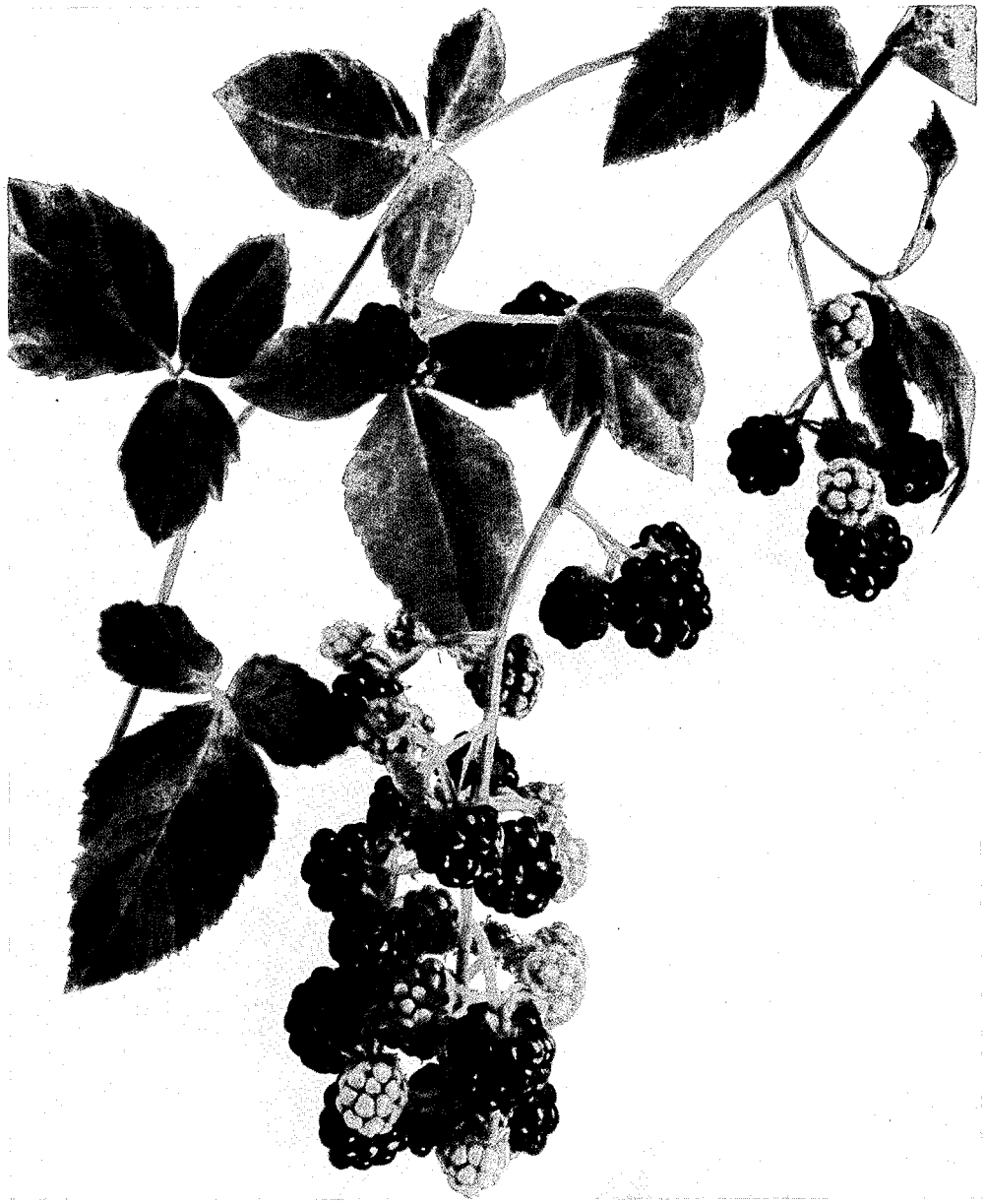
Inventor
M. B. Crane
by Robb & Robb
Attorneys Patented Mar. 9, 1943

UNITED STATES PATENT OFFICE

571

BLACKBERRY PLANT

Morley B. Crane, Merton Park, London, England, assignor to Armstrong Nurseries, Inc., Ontario, Calif., a corporation of California Application October 20, 1942, Serial No. 462,738

1 Claim. (Cl. 47—62)

The present invention relates to a new and distinct variety of blackberry plant, originated by crossing John Innes Blackberry, a thorny type, with a thornless seedling resulting from selfing John Innes Blackberry, which bears inferior or worthless fruit.

This new variety is characterized as to novelty in numerous respects, among which the following are dominantly important:

(1) The complete lack of prickles or thorns, either on the back of the leaves or on the canes.

(2) The distinctive flavor of the berry, which is rich and sweet and is somewhat reminiscent of the flavor of the fruit of *Morus nigra*.

(3) Its ripening season, which is mid-season and occurs over a long period of time as compared with other blackberries.

(4) The large size and round shape of its fruit, which when ripe is black in color.

(5) The large size of the drupelets.

(6) Its vigorous habit of growth.

(7) Its ability to produce satisfactory fruit from laterals on two-year-old as well as one-year-old canes in a mild climate such as Ontario, California.

(8) Its tetraploid chromosome arrangement of the somatic number of 28 chromosomes.

Asexual reproduction of this new variety by layering and tipping shows the foregoing characteristics come true to form and are established.

The following is a detail description of the new variety, the color terminology therein according with "Robert F. Wilson Horticultural Color Chart."

(Observations from specimens grown at Mostyn Road, Merton Park, London, England.)

Plant: Medium size; vigorous; rambling; half-hardy; productive; regular bearer; deciduous; not dying back each year in milder climates, but old growth should be removed after fruiting.

Environment: Sun; climate, dry or moist.

Canes: Slender; trailing; smooth.

*Color.*—On side exposed to sun, near Maroon (Plate $_{10}$30, p. 185). When observed under magnifying glass where tomentum is rubbed off, laid over a ground color of near Pea Green (Plate 61/2, p. 61) which shows at irregular intervals on side of younger cane. On side where it is protected from sun, older canes near Maroon (Plate $_{10}$30, p. 185).

Thorns or prickles: None.

New shoots:

*Color.*—Under magnifying glass, on side exposed to sun near Maroon (Plate $_{10}$30, p. 185) but near tip near Garnet Lake (Plate $_{8}$28, p. 172), much covered by tomentum. Side protected from sun near Scheeles Green (Plate $_{8}$60/3, p. 175).

*Large prickles.*—None.

*Small prickles.*—None.

*Tomentum.* — Much. — *Color* — near white when young, changing to Straw Yellow (Plate $_{6}$04/3, p. 67) with age.

*Bloom.*—None.

Foliage:

*Leaves.*—Compound of three.

*Leaflets.*—Moderately sparse; medium size; moderately leathery; fairly smooth and flat. *Shape*—ovate with apex acute. *Base*—rounded, often slightly cuneate. *Margin*—simply serrate at base; dentate from middle to apex. *Color*—mature, upper surface—near Parsley Green (Plate $_{009}$62, p. 193); under surface—near Willow Green, (Plate $_{000}$862, p. 199). *Measurements*—terminal leaflet—6½ to 8½ cm. from base to apex; 4½ to 5½ cm. in breadth; pair of basal leaflets 3½ to 5½ cm. in length and 3 to 4 cm. in breadth. *Color*—young, upper surface—near Lettuce Green, (Plate $_{8}$61, p. 176), except at margins where teeth are heavily colored with Maroon, (Plate $_{10}$30, p. 185); under surface—near Spinach Green (Plate $_{09}$60./2, p. 187), except at near margins where teeth are heavily colored with Maroon (Plate $_{10}$30, p. 185). *Variations*—some veins and midrib often colored with Maroon (Plate $_{10}$30, p. 185) for at least part of their length.

Rachis: (The supporting stem of the compound leaf)—light. Upper side—hairy and tomentose; under side—hairy and tomentose.

Stipules: Moderately short; very narrow; recurved toward stem.

Flowers borne: 15 to 50 to stem in irregular cluster, on normal, long panicle, with mostly cymose branches; perfect; complete.

*Quantity of bloom.*—Free when properly pruned.

*Continuity.*—One season.

Flower:

*Pedicel.*—Short to medium; medium heavy; stiff; much tomentum; completely covered with woolly tomentum which is White at first but soon turns to Straw Yellow (Plate $_{6}$04/3, p. 67).

*Before calyx breaks.*—*Size*—medium to large. *Form*—ovoid; tomentose on the surface of the bud.

Bloom: Large; 2½ cm. to 3½ cm. in diameter.

*Petalage.*—Single.

*Form.*—Flat with individual petals slightly cupped.

Petals: Thin.

*Color.*—Outside surface—a shade of Pink. Inside surface—a shade of Pink.

*Reproductive organs*

Stamens: Many.
Filaments: Medium to long; most with anthers.
Anthers: Medium to large.
Pollen: Abundant.
Pistils: Medium number, somewhat long.
Sepals: Persistent; moderately short; slightly recurved.
Fruit: Maturity when described—ripe.
*Size of berry.*—¾ to 1¼ inches in length; fairly uniform. *Diameter*—⅝ to ⅞ inches. *Number of clusters*—many when lateral branches are pruned to two eyes. *Number of berries to clusters*—15 to 50.
*Form of Drupelets.*—Uniform; symmetrical; broadly oval, often nearly round from outside appearance; very large. *Drupelets*—persist to torus.
*Sterility.*—Highly fertile.
*Skin.*—Thin; tender; black in color when ripe.
*Tomentum.*—Bloom or hairs; wanting.
*Ripens.*—Uneven over moderately long season.
*Texture.*—Firm with medium-sized soft seeds.
*Flavor.*—Mild; delicate; sweet, with hint of Mulberry flavor.
*Aroma.*—Not pronounced.
*Eating quality.*—Excellent.
*Cooking quality.*—Fair.
Seed:
*Size.*—Medium.
*Length.*—2 to 3 mm.
*Breadth.*—1½ to 2 mm.
*Form.*—Often cuneate toward base; irregular; many somewhat kidney shaped.
Use: Market; local; dessert; culinary.
Keeping quality: Medium.
Shipping quality: Medium. Berry holds shape on picking; picks from pedicel easily.
Disease: Resistant to mildew; rust; blight; berry mite.

I claim:

A new and distinct variety of blackberry plant, characterized as to novelty by complete absence of prickles or thorns; distinctive flavor, large size and round shape of the fruit; its midseason ripening and continuity over a long period of time; the large size of the drupelets; the vigorous habit of growth of the plant; production of satisfactory fruit from laterals on both two and one year old canes; and its tetraploid chromosome arrangement, substantially as shown and described.

MORLEY B. CRANE.